United States Patent
Ahn et al.

(10) Patent No.: US 10,615,450 B2
(45) Date of Patent: Apr. 7, 2020

(54) ELECTROLYTE SOLUTION FOR LITHIUM SECONDARY BATTERY AND LITHIUM SECONDARY BATTERY INCLUDING THE SAME

(71) Applicant: LG Chem, Ltd., Seoul (KR)

(72) Inventors: Kyoung Ho Ahn, Daejeon (KR); Yu Ra Jeong, Daejeon (KR); Chul Haeng Lee, Daejeon (KR); Young Min Lim, Daejeon (KR); Jeong Woo Oh, Daejeon (KR); Jung Hoon Lee, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 16/073,012

(22) PCT Filed: Oct. 13, 2017

(86) PCT No.: PCT/KR2017/011352
§ 371 (c)(1),
(2) Date: Jul. 26, 2018

(87) PCT Pub. No.: WO2018/070846
PCT Pub. Date: Apr. 19, 2018

(65) Prior Publication Data
US 2019/0036155 A1    Jan. 31, 2019

(30) Foreign Application Priority Data
Oct. 14, 2016  (KR) .................. 10-2016-0133811
Oct. 13, 2017  (KR) .................. 10-2017-0133267

(51) Int. Cl.
*H01M 10/052*  (2010.01)
*H01M 10/0525* (2010.01)
*H01M 10/0567* (2010.01)
*C07C 265/02*  (2006.01)
*C07C 265/10*  (2006.01)
*C07C 265/12*  (2006.01)
*H01M 4/02*    (2006.01)
*H01M 10/0568* (2010.01)
*H01M 10/0569* (2010.01)

(52) U.S. Cl.
CPC ....... *H01M 10/0525* (2013.01); *C07C 265/02* (2013.01); *C07C 265/10* (2013.01); *C07C 265/12* (2013.01); *H01M 4/02* (2013.01); *H01M 10/0567* (2013.01); *H01M 10/0568* (2013.01); *H01M 10/0569* (2013.01); *H01M 2004/027* (2013.01); *H01M 2004/028* (2013.01)

(58) Field of Classification Search
CPC ............... H01M 4/02; H01M 10/0525; H01M 10/0567; H01M 10/568; H01M 10/0569; H01M 2004/027; H01M 2004/028; H01M 10/0568; C07C 265/02; C07C 265/10; C07C 265/12
USPC .................................................. 429/231.95
See application file for complete search history.

(56) References Cited

U.S. PATENT DOCUMENTS

| | | | |
|---|---|---|---|
| 10,381,685 B2 * | 8/2019 | Ahn | ........... C07C 265/02 |
| 2004/0029012 A1 * | 2/2004 | Tanizaki | ........... H01M 4/131 429/231.95 |
| 2007/0059588 A1 | 3/2007 | Lee et al. | |
| 2009/0130566 A1 | 5/2009 | Iwanaga et al. | |
| 2011/0223489 A1 | 9/2011 | Iwanaga et al. | |
| 2013/0059210 A1 * | 3/2013 | Yu | ........... H01M 4/13 429/338 |
| 2015/0333370 A1 | 11/2015 | Abe et al. | |
| 2017/0294682 A1 | 10/2017 | Ann et al. | |

FOREIGN PATENT DOCUMENTS

| | | |
|---|---|---|
| EP | 2369671 A1 | 9/2011 |
| JP | 2000-195545 A | 7/2000 |
| JP | 2014-146558 A | 8/2014 |
| KR | 100746479 B1 | 8/2007 |
| WO | 2016-053040 A1 | 4/2016 |

OTHER PUBLICATIONS

International Search Report for Application No. PCT/KR2017/011352 dated Jan. 22, 2018.

* cited by examiner

*Primary Examiner* — Amanda C. Walke
(74) *Attorney, Agent, or Firm* — Lerner, David, Littenberg, Krumholz & Mentlik, LLP

(57) ABSTRACT

The present invention provides an electrolyte solution for a lithium secondary battery including an additive, which may prevent a chemical reaction between the electrolyte solution and an electrode by forming a stable solid electrolyte interface (SEI) and a protection layer on the surface of the electrode, and a lithium secondary battery in which life characteristics and high-temperature stability are improved by including the same.

5 Claims, No Drawings

ELECTROLYTE SOLUTION FOR LITHIUM SECONDARY BATTERY AND LITHIUM SECONDARY BATTERY INCLUDING THE SAME

CROSS-REFERENCE TO RELATED APPLICATIONS

The present application is a national phase entry under 35 U.S.C. § 371 of International Application No. PCT/KR2017/011352, filed on Oct. 13, 2017, which claims the benefit of Korean Patent Application Nos. 10-2016-0133811, filed on Oct. 14, 2016, and 10-2017-0133267, filed on Oct. 13, 2017, the disclosures of which are incorporated herein by reference.

Technical Field

The present invention relates to an electrolyte solution for a lithium secondary battery, which may secure low initial resistance characteristics and high-temperature durability of the lithium secondary battery, and a lithium secondary battery including the same.

Background Art

In line with the increased use of portable electronic devices due to the recent development of high-tech electronics industry, the need for batteries having high energy density as power sources of these portable electronic devices is increasing.

A battery is a device that converts chemical energy generated during an electrochemical redox reaction of a chemical material included in the battery into electrical energy, wherein the battery may be categorized into a primary battery, which is discarded when the energy in the battery is all consumed, and a secondary battery which may be charged many times. In particular, the secondary battery is advantageous in that it may be used by being charged and discharged many times by reversible interconversion of the chemical energy and the electrical energy.

Among these secondary batteries, lithium secondary batteries have been variously used as driving power sources of portable devices such as video cameras, mobile phones, and notebook computers, because the lithium secondary battery is advantageous in that recharging is possible, energy density per unit weight is more than three times higher than that of a conventional lead-acid battery, a nickel-cadmium battery, a nickel-hydrogen battery, or a nickel-zinc battery, and fast charging is possible.

A lithium secondary battery is prepared by injecting an electrolyte solution into a battery cell including an electrode assembly in which a positive electrode including a positive electrode active material capable of intercalating and deintercalating lithium and a negative electrode including a negative electrode active material capable of intercalating and deintercalating lithium are stacked.

In this case, a non-aqueous organic solvent having high voltage stability, high ionic conductivity and permittivity, and low viscosity has been used as the electrolyte solution. Specifically, in a case in which a carbonate-based polar non-aqueous solvent is used as the non-aqueous organic solvent, an irreversible reaction, in which charges are excessively used due to a side reaction between the electrolyte solution and the negative electrode/positive electrode, proceeds during initial charge, and a passivation layer, such as a solid electrolyte interface (hereinafter, referred to as "SEI"), is formed on the surface of the negative electrode and a protection layer is formed on the surface of the positive electrode by the irreversible reaction.

The SEI film and the protection layer may prevent the decomposition of the electrolyte solution during charge and discharge and may act as an ion tunnel.

Thus, in order to improve life characteristics and performance of the secondary battery, demand for the development of an electrolyte solution having a novel configuration has been increased.

PRIOR ART DOCUMENT

Japanese Patent Application Laid-open Publication No. JP 2000-195545

DISCLOSURE OF THE INVENTION

Technical Problem

An aspect of the present invention provides an electrolyte solution for a lithium secondary battery including an electrolyte solution additive which may form a protection layer on the surface of a positive electrode as well as a stable solid electrolyte interface (SEI) on the surface of a negative electrode during initial charge.

Another aspect of the present invention provides a lithium secondary battery including the electrolyte solution for a lithium secondary battery of the present invention.

Technical Solution

According to an aspect of the present invention,
there is provided an electrolyte solution for a lithium secondary battery including an electrolyte salt, an organic solvent, and an additive,
wherein the additive includes a compound represented by Formula 1:

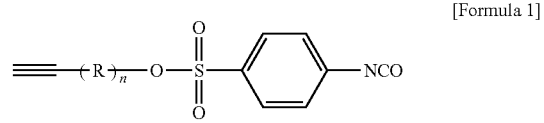

[Formula 1]

wherein, in Formula 1,
R is an alkylene group having 1 to 5 carbon atoms or an arylene group having 5 to 8 carbon atoms, and
n is an integer of 1 to 10.

The compound represented by Formula 1 may include at least one selected from the group consisting of compounds represented by Formulae 1a to 1c.

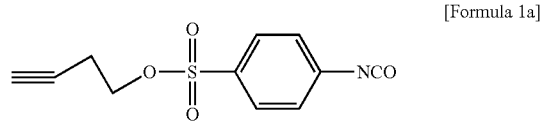

[Formula 1a]

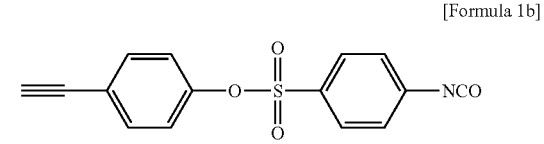

[Formula 1b]

-continued

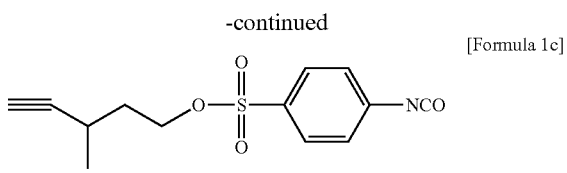

[Formula 1c]

The compound represented by Formula 1 may be included in an amount of 0.05 wt % to 7 wt %, for example, 0.1 wt % to 5 wt %, based on a total weight of the electrolyte solution for a lithium secondary battery.

According to another aspect of the present invention, there is provided a lithium secondary battery including a positive electrode, a negative electrode, a separator disposed between the positive electrode and the negative electrode, and the electrolyte solution for a lithium secondary battery of the present invention.

Advantageous Effects

According to the present invention, an electrolyte solution for a lithium secondary battery including an additive, which may form a protection layer on a surface of a positive electrode as well as a stable solid electrolyte interface (SEI) on a surface of a negative electrode during initial charge to prevent decomposition of the surface of the electrode and an oxidation reaction of the electrolyte solution during high-temperature storage, may be provided. Also, a lithium secondary battery, which may exhibit excellent high-temperature storage characteristics and life characteristics as well as low initial resistance, may be prepared by including the electrolyte solution.

MODE FOR CARRYING OUT THE INVENTION

Hereinafter, the present invention will be described in more detail. In this case, it will be understood that words or terms used in the specification and claims should be interpreted as having a meaning that is consistent with their meaning in the context of the relevant art and the technical idea of the invention, based on the principle that an inventor may properly define the meaning of the words or terms to best explain the invention, and the following description is not to be construed as limiting the scope of the present invention.

Before describing the present invention, the expressions "a" and "b" in the description of "a to b carbon atoms" in the specification each denote the number of carbon atoms included in a specific functional group. That is, the functional group may include "a" to "b" carbon atoms. For example, the expression "alkylene group having 1 to 5 carbon atoms" denotes an alkylene group including 1 to 5 carbon atoms, that is, —$CH_2$—, —$CH_2CH_2$—, —$CH_2CH_2CH_2$—, —$CH_2(CH_2)CH$—, —$CH(CH_2)CH_2$—, and —$CH(CH_2)CH_2CH_2$—.

Also, in the present specification, the expression "alkylene group" denotes a branched or unbranched aliphatic hydrocarbon group or a functional group in the form in which one hydrogen atom is missing from carbon atoms located at both ends of the aliphatic hydrocarbon group. In an embodiment, the alkylene group may be substituted or unsubstituted. The alkylene group includes a methylene group, an ethylene group, a propylene group, an isopropylene group, a butylene group, an isobutylene group, a tert-butylene group, a pentylene group, and a 3-pentylene group, but the present invention is not limited thereto, and each thereof may be selectively substituted in another exemplary embodiment.

Furthermore, in the present specification, the expression "arylene group" denotes an aromatic hydrocarbon group having a $C_nH_{2n-1}$ structure, in which one hydrogen atom is subtracted from aliphatic hydrocarbon, or a functional group in the form in which a hydrogen atom is separated from the aromatic hydrocarbon. In an embodiment, the arylene group includes a phenylene group, a biphenylene group, a terphenylene group, a naphthylene group, and a phenanthrylene group, but the present invention is not limited thereto, and each thereof may be selectively substituted in another exemplary embodiment.

With respect to a lithium secondary battery known to date, it has been difficult to prevent corrosion of a metallic material, and, particularly, it has been insufficient to maintain performance at an acceptable level under extreme conditions such as overcharge, overdischarge, and high-temperature storage. Thus, in the present invention, since an electrolyte solution for a lithium secondary battery, which includes an additive capable of forming a solid electrolyte interface (SEI) having improved thermal stability on a surface of an electrode, is provided, a lithium secondary battery having low initial resistance and improved high-temperature durability may be prepared by preventing a chemical reaction between the electrolyte solution and the electrode.

Hereinafter, the present invention will be described in detail according to exemplary embodiments.

Specifically, in an embodiment of the present invention, provided is an electrolyte solution for a lithium secondary battery which includes an electrolyte salt, an organic solvent, and an additive, wherein the additive includes a compound represented by Formula 1 below.

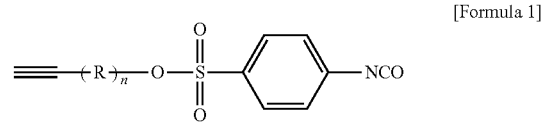

[Formula 1]

In Formula 1,

R is an alkylene group having 1 to 5 carbon atoms or an arylene group having 5 to 8 carbon atoms, and n is an integer of 1 to 10.

First, in the electrolyte solution for a lithium secondary battery according to the embodiment of the present invention, any electrolyte salt typically used in an electrolyte solution for a lithium secondary battery may be used as the above electrolyte salt without limitation, and, for example, the lithium salt may include $Li^+$ as a cation, and may include at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$ as an anion. Specifically, the lithium salt may include a single material selected from the group consisting of LiCl, LiBr, LiI, $LiClO_4$, $LiBF_4$, $LiB_{10}Cl_{10}$, $LiPF_6$, $LiCF_3SO_3$, $LiCH_3CO_2$, $LiCF_3CO_2$, $LiAsF_6$, $LiSbF_6$, $LiAlCl_4$, $LiAlO_4$, and $LiCH_3SO_3$, or a mixture of two or more thereof, and, in addition thereto, an electrolyte salt, such as a lithium imide salt represented by lithium bisperfluoroethanesulfonimide (LiBETI, LiN($SO_2C_2F_5$)$_2$), lithium fluorosulfonyl imide (LiFSI, LiN($SO_2F$)$_2$), and lithium (bis)trifluoromethanesulfonimide (LiTFSI, LiN($SO_2CF_3$)$_2$) which are typically used in the electrolyte solution of the lithium secondary battery, may be used without limitation. Specifically, the electrolyte salt may include a single material selected from the group consisting of $LiPF_6$, $LiBF_4$, $LiCH_3CO_2$, $LiCF_3CO_2$, $LiCH_3SO_3$, LiFSI, LiTFSI, and LiN($C_2F_5SO_2$)$_2$, or a mixture of two or more thereof.

The electrolyte salt may be appropriately changed in a normally usable range, but may be included in a concentration of 0.8 M to 1.5 M in the electrolyte solution to obtain an optimum effect of forming an SEI film for preventing corrosion of the surface of the electrode. In a case in which the concentration of the electrolyte salt is greater than 1.5 M, the effect of forming the SEI film may be reduced.

Also, in the electrolyte solution for a lithium secondary battery of the present invention, the organic solvent is not limited as long as it may minimize decomposition due to an oxidation reaction during charge and discharge of the battery and may exhibit desired characteristics with the additive. For example, an ether-based solvent, an ester-based solvent, or an amide-based solvent may be used alone or in mixture of two or more thereof.

As the ether-based solvent among the organic solvents, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

Furthermore, the ester-based solvent may include at least one compound selected from the group consisting of a cyclic carbonate compound, a linear carbonate compound, a linear ester compound, and a cyclic ester compound.

Among these compounds, specific examples of the cyclic carbonate compound may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof.

Also, specific examples of the linear carbonate compound may be any one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof, but the present invention is not limited thereto.

Specific examples of the linear ester compound may be any one selected from the group consisting of methyl acetate, ethyl acetate, propyl acetate, methyl propionate, ethyl propionate, propyl propionate, and butyl propionate, or a mixture of two or more thereof, but the present invention is not limited thereto.

Specific examples of the cyclic ester compound may be any one selected from the group consisting of γ-butyrolactone, γ-valerolactone, γ-caprolactone, δ-valerolactone, and ε-caprolactone, or a mixture of two or more thereof, but the present invention is not limited thereto.

Among the ester-based solvents, since the cyclic carbonate-based compound is well dissociate the lithium salt in the electrolyte due to high permittivity as a highly viscous organic solvent, the cyclic carbonate-based compound may be preferably used. An electrolyte solution having high electrical conductivity may be prepared when the above cyclic carbonate-based compound is mixed with the linear carbonate-based compound having the low viscosity and low permittivity, such as dimethyl carbonate and diethyl carbonate, in an appropriate ratio. Therefore, the mixed compound may be more preferably used.

Also, in the electrolyte solution for a lithium secondary battery according to the embodiment of the present invention, the compound represented by Formula 1, which is included as the additive, may include at least one selected from the group consisting of compounds represented by the following Formulae 1a to 1c.

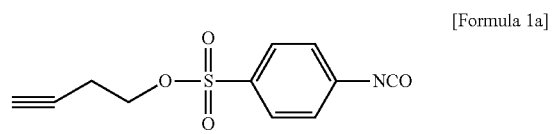
[Formula 1a]

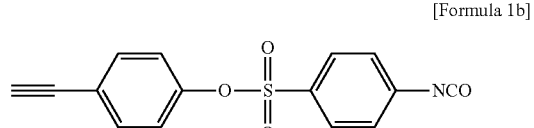
[Formula 1b]

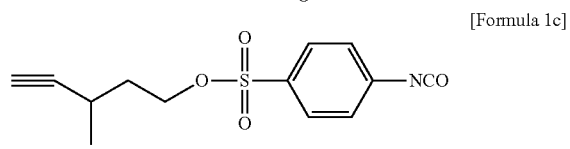
[Formula 1c]

In the electrolyte solution for a lithium secondary battery according to the embodiment of the present invention, the additive may be included in an amount of 0.05 wt % to 7 wt %, for example, 0.1 wt % to 5 wt %, based on a total weight of the electrolyte solution.

In a case in which the compound represented by Formula 1 is included within the above range, a secondary battery having more improved overall performance may be prepared. For example, in a case in which the amount of the additive is 0.05 wt % or more, a more stable SEI film may be formed on the surface of the negative electrode and a protection layer may be formed on the surface of the positive electrode during the initial charge. In a case in which the amount of the additive is 7 wt % or less, high-temperature durability, for example, a gas generation suppression effect, may be achieved more effectively while suppressing a decrease in capacity and an increase in resistance due to a side reaction.

In general, a lithium secondary battery is disadvantageous in that the SEI film formed on the surface of the negative electrode gradually collapses due to electrochemical energy and thermal energy which are increased over time when the lithium secondary battery in a fully charged state is stored at high temperature (e.g. left standing for 4 days at 60° C. after charged to 100% at 4.2 V). In this case, a side reaction, in which the carbonate-based solvent in the surrounding electrolyte solution is reacted with the surface of the negative electrode exposed due to the collapse of the interface and decomposed, continuously occurs.

The side reaction may continuously generate gases, wherein the main gases generated in this case include CO, $CO_2$, $CH_4$, and $C_2H_6$. The main gases generated may vary depending on the type of carbonate used as the electrolyte solution solvent and the type of a negative electrode active material, and, regardless of the type, the continuous gas generation increases an internal pressure of the lithium secondary battery at high temperature to cause battery thickness swelling.

Thus, in the present invention, since the compound represented by Formula 1, which contains all of a propargyl group having a triple bond, a sulfonate group, and an isocyanate group which are known to be easily bonded with metal ions, is included as the electrolyte solution additive, the more stable SEI film on the surface of the negative electrode and the protection layer on the surface of the positive electrode are formed faster during the initial charge to suppress the corrosion of the surfaces of the positive electrode and negative electrode and the decomposition of the carbonate-based organic solvent, and thus, low initial resistance may be realized and, simultaneously, the swelling of the battery during high-temperature storage after full charge may be more effectively suppressed. Therefore, a lithium secondary battery having improved high-temperature durability may be prepared.

Specifically, since the compound represented by Formula 1, which is included as the additive, contains an unsaturated functional group, such as a triple bond, or polar functional group as a substituent, bonding with metal ions is not only easy, but it may also more easily accept electrons from the negative electrode in comparison to a polar solvent. Thus, it may first be reduced at a lower voltage than the polar solvent. That is, the unsaturated functional group or polar functional group contained in the compound represented by Formula 1 may be more easily reduced and/or decomposed by radicals and/or ions during charge, and, in this case, the unsaturated functional group or polar functional group may precipitate or form an insoluble compound by bonding with lithium ions. The insoluble compound may react with various functional groups present on the surface of a carbon-based negative electrode or with the carbon-based negative electrode itself to form a covalent bond or to be adsorbed on the surface of the negative electrode. By the bonding or the adsorbing, an SEI film having improved stability, which may be maintained in a stable state even after a long period of charge and discharge, is formed on the surface of the negative electrode. Since the stable SEI film may effectively reduce or prevent the penetration of the electrolyte solution, the gas generated during the high-temperature storage may be reduced.

Also, since the compound represented by Formula 1 contains the isocyanate group as a substituent, the compound may first be oxidized and/or decomposed in comparison to the polar solvent during the charge. For example, as in the following Reaction Formula 1, the compound represented by Formula 1 may form a protection layer composed of a complex on the surface of the positive electrode by reacting with a reaction group present on the surface of the electrode, i.e., a hydroxyl group which is derived from lithium hydroxide used for the preparation of a positive electrode active material or derived from metal oxide. The protection layer formed on the surface of the positive electrode by the complex is maintained in a stable state for a long period of time after the charge and discharge, and thus, stability may be secured.

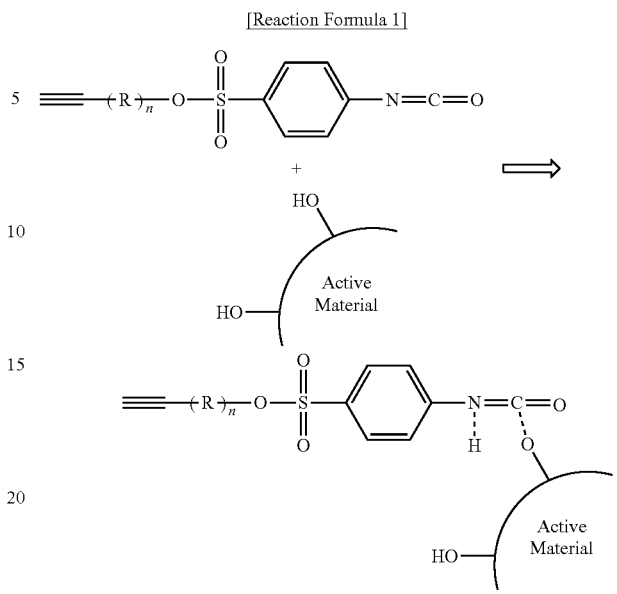

[Reaction Formula 1]

Furthermore, the compound represented by Formula 1 reacts with the hydroxyl group on the surfaces of the positive electrode and the negative electrode under extreme conditions, such as overcharge, overdischarge, and high-temperature storage, to form an anion as in the following Reaction Formula 2, and the formed anion may form a coordination bond with a positively charged metallic element among metallic components of the positive electrode active material or negative electrode active material to form an SEI film, such as a passivation layer, on the surface of the negative electrode or form a protection layer on the surface of the positive electrode. It is possible to prevent the surfaces of the positive electrode and negative electrode from being exposed to the electrolyte solution. As a result, the chemical reaction between the electrolyte solution and the positive electrode or negative electrode may be suppressed. Thus, the decomposition or corrosion of the surface of the positive electrode or negative electrode under the extreme conditions may be prevented.

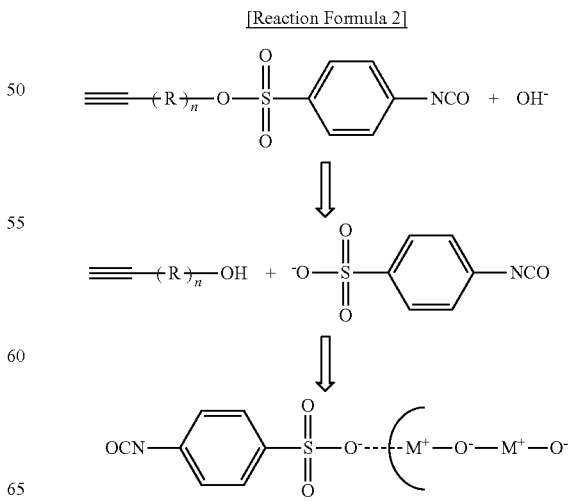

[Reaction Formula 2]

As described above, the stable SEI film formed on the surface of the negative electrode and the stable protection layer formed on the surface of the positive electrode by the compound represented by Formula 1, which is included as the electrolyte solution additive of the present invention, may effectively block the penetration of the organic solvent, in which lithium ions are solvated during the intercalation of the lithium ions, into the electrode. Thus, since the SEI film and the protection layer may more effectively block a direct contact between the organic solvent and the positive electrode and/or negative electrode, reversibility of the intercalation/deintercalation of lithium ions is further improved, and, as a result, a lithium secondary battery, which may exhibit a high-temperature durability improvement effect as well as low initial resistance, may be prepared.

Also, the electrolyte solution for a lithium secondary battery according to the embodiment of the present invention may further include an additive for forming an SEI film, if necessary. As the additive for forming an SEI film which may be used in the present invention, vinylene carbonate (VC), vinyl ethylene carbonate, fluoroethylene carbonate, cyclic sulfite, saturated sultone, unsaturated sultone, and a non-cyclic sulfone may be used alone or in a mixture of two or more thereof.

In this case, the cyclic sulfite may include ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite, and 1,3-butylene glycol sulfite, the saturated sultone may include 1,3-propane sultone and 1,4-butane sultone, the unsaturated sultone may include ethene sultone, 1,3-propene sultone, 1,4-butene sultone, and 1-methyl-1,3-propene sultone, and the non-cyclic sulfone may include divinyl sulfone, dimethyl sulfone, diethyl sulfone, methyl ethyl sulfone, and methyl vinyl sulfone.

The additive for forming an SEI film may be included in an amount of 10 wt % or less based on the total weight of the electrolyte solution to form an excellent SEI film, and may be specifically included in an amount of 0.5 wt % to 10 wt % to prevent the occurrence of a side reaction due to the excessive addition.

In conclusion, with respect to the electrolyte solution for a lithium secondary battery of the present invention, since the compound represented by Formula 1, which contains all the triple bond structure, the sulfonate group, and the isocyanate group (—NCO) in the compound, is included as the electrolyte solution additive, a stable protection layer on the surface of the positive electrode and a stable SEI film on the surface of the negative electrode may be formed to significantly improve the high-temperature durability of the lithium secondary battery even under extreme conditions such as high-temperature storage.

Furthermore, in the present invention, provided is a lithium secondary battery including a positive electrode, a negative electrode, a separator disposed between the positive electrode and the negative electrode, and an electrolyte solution, wherein the lithium secondary battery includes the electrolyte solution for a lithium secondary battery of the present invention as the electrolyte solution.

First, the positive electrode may be prepared by forming a positive electrode material mixture layer on a positive electrode collector. The positive electrode material mixture layer may be prepared by coating the positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may specifically include a lithium composite metal oxide including lithium and at least one metal such as cobalt, manganese, nickel, or aluminum. Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$), etc.), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$), etc.), or lithium-nickel-cobalt-transition metal (M) oxide (e.g., $Li(Ni_{p2}Co_{q2}Mn_{r3}M_{S2})O_2$(where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), etc.), and any one thereof or a compound of two or more thereof may be included.

Among these materials, in terms of the improvement of capacity characteristics and stability of the battery, the lithium composite metal oxide may include $LiCoO_2$, $LiMnO_2$, $LiNiO_2$, lithium nickel manganese cobalt oxide (e.g., $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$ or $Li(Ni_{0.8}Mn_{0.1}Co_{0.1})O_2$) or lithium nickel cobalt aluminum oxide (e.g., $LiNi_{0.8}Co_{0.15}Al_{0.05}O_2$, etc.).

The positive electrode active material may be included in an amount of 40 wt % to 90 wt %, for example, 40 wt % to 75 wt % based on a total weight of solid content in the positive electrode slurry.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

The conductive agent is commonly added in an amount of 1 wt % to 30 wt % based on the total weight of the solid content in the positive electrode slurry.

Any conductive agent may be used without particular limitation so long as it has conductivity without causing adverse chemical changes in the battery, and, for example, a conductive material such as: graphite; a carbon-based material such as carbon black, acetylene black, Ketjen black, channel black, furnace black, lamp black, and thermal black; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives may be used. Specific examples of a commercial conductive agent may include acetylene black-based products (Chevron Chemical Company, Denka black (Denka Singapore Private Limited), or Gulf Oil Company), Ketjen black, ethylene carbonate (EC)-based products (Armak Company), Vulcan XC-72 (Cabot Company), and Super P (Timcal Graphite & Carbon).

The solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 10 wt % to 70 wt %, for example, 20 wt % to 60 wt %.

Also, the negative electrode may be prepared by forming a negative electrode material mixture layer on a negative electrode collector. The negative electrode material mixture layer may be formed by coating the negative electrode collector with a slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material. The negative electrode collector may be used in various shapes such as a film, a sheet, a foil, a net, a porous body, a foam body, a non-woven fabric body, and the like.

Furthermore, the negative electrode active material includes a material capable of reversibly intercalating/deintercalating lithium ions, lithium metal, an alloy of the lithium metal, a metal composite oxide, a material which may be doped and undoped with lithium, or a transition metal oxide.

As the material capable of reversibly intercalating/deintercalating lithium ions, any carbon material may be used so long as it is a carbon-based negative electrode active material generally used in a lithium ion secondary battery, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the alloy of the lithium metal, an alloy of metal selected from the group consisting of sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn) may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \le x \le 1$), $Li_xWO_2$ ($0 \le x \le 1$), and $Sn_xMe_{1-x}Me'_yO_z$ (Me: manganese (Mn), Fe, Pb, or Ge; Me': Al, boron (B), phosphorus (P), Si, Groups I, II and III elements of the periodic table, or halogen; $0<x\le1$; $1\le y\le3$; $1\le z\le8$) may be used as the metal composite oxide.

The material, which may be doped and undoped with lithium, may include Si, $SiO_x$ ($0<x<2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, radium (Ra), scandium (Sc), yttrium (Y), Ti, zirconium (Zr), hafnium (Hf), rutherfordium (Rf), V, niobium (Nb), tantalum (Ta), dubidium (Db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), copper (Cu), silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), polonium (Po), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and, for example, a conductive material, such as: graphite such as natural graphite or artificial graphite; carbon black such as acetylene black, Ketjen black, channel black, furnace black, lamp black, and thermal black; conductive fibers such as carbon fibers and metal fibers; metal powder such as fluorocarbon powder, aluminum powder, and nickel powder; conductive whiskers such as zinc oxide whiskers and potassium titanate whiskers;

conductive metal oxide such as titanium oxide; or polyphenylene derivatives, may be used.

The solvent may include water or an organic solvent, such as N-methyl-2-pyrrolidone (NMP) and alcohol, and may be used in an amount such that desirable viscosity is obtained when the negative electrode active material as well as selectively the binder and the conductive agent are included. For example, the solvent may be included in an amount such that a concentration of the solid content in the slurry including the negative electrode active material as well as selectively the binder and the conductive agent is in a range of 50 wt % to 75 wt %, for example, 50 wt % to 65 wt %.

Also, the separator plays a role in blocking an internal short circuit between both electrodes and impregnating the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 μm to 50 μm and a porosity of 5% to 95%. Also, the porous separator may generally have a thickness of 5 μm to 300 μm.

A shape of the lithium secondary battery of the present invention is not particularly limited, but a cylindrical type using a can, a prismatic type, a pouch type, or a coin type may be used.

After disposing an electrode assembly, which is formed by sequentially stacking a positive electrode, a negative electrode, and a separator disposed between the positive electrode and the negative electrode, in a battery case, the secondary battery of the present invention may be prepared by injecting and impregnating the electrolyte solution for a lithium secondary battery of the present invention and then performing a formation process. Furthermore, before or after the formation process of the secondary battery of the present invention, an urethane reaction effect between an —NCO group, as an end group of the compound represented by Formula 1, and an OH group, as an impurity on the surface of the electrode, is further increased by performing an aging process at room temperature or high temperature, and thus, it is thought that the effect of forming the SEI film on the surface of the negative electrode and the effect of forming the protection layer on the surface of the positive electrode may be further improved. Thus, since the electrode corrosion may be prevented by preventing the surface of the electrode from being exposed even under the extreme conditions such as overcharge, overdischarge, and high-temperature storage, the initial resistance of the lithium secondary battery may be reduced and the high-temperature durability may be improved.

While specific embodiments have been described in the detailed descriptions of the present invention as described above. However, various modifications may be provided without departing from the spirit and scope of the present invention. Therefore, the scope of the present invention is defined not by the described embodiment but by the appended claims, and encompasses equivalents that fall within the scope of the appended claims.

EXAMPLES

Example 1

(Electrolyte Solution Preparation)

An electrolyte solution for a lithium secondary battery of the present invention was prepared by adding 3 g of VC and 0.05 g of the compound of Formula 1a to 96.95 g of a mixed solution of ethylene carbonate (EC): ethyl methyl carbonate (EMC): diethyl carbonate (DEC) (30:50:20 vol %) in which 1 M $LiPF_6$ was dissolved (see Table 1 below).

(Negative Electrode Preparation)

Natural graphite, a styrene-butadiene rubber (SBR) (ZEON) as a binder and carboxymethylcellulose (CMC, NIPPON A&L) were added to distilled water at a ratio of 98:1.0:1.0 (wt %) and stirred for 60 minutes using a mechanical stirrer to prepare a negative electrode active material slurry having a solid content of 85 wt %. After a 10 μm thick copper current collector was coated with the slurry to a thickness of about 60 μm using a doctor blade and dried for 0.5 hours in a hot air dryer at 100° C., the coated copper current collector was again dried at 120° C. under vacuum for 4 hours and roll-pressed to prepare a negative electrode plate.

(Positive Electrode Preparation)

$LiNi_{0.6}Mn_{0.2}Co_{0.2}O_2$, artificial graphite powder (SFG6, Timcal) and carbon black (Ketjen black, ECP) as a conductive agent, and a modified acrylonitrile rubber (BM-720H, Zeon Corporation) and polyvinylidene fluoride (S6020 and S5130, manufactured by Solvay) as a binder were added to an N-methyl-2-pyrrolidone solvent at a ratio of 80:2.5:6.5:2.5:5.8 (wt %) and then stirred for 30 minutes using a mechanical stirrer to prepare a positive electrode active material slurry having a solid content of 85 wt %. After a 20 μm thick aluminum current collector was coated with the slurry to a thickness of about 60 μm using a doctor blade and dried for 0.5 hours in a hot air dryer at 100° C., the coated copper current collector was again dried at 120° C. under vacuum for 4 hours and roll-pressed to prepare a positive electrode plate.

(Secondary Battery Preparation)

An electrode assembly was prepared by disposing a porous polyethylene separator between the prepared negative electrode and positive electrode, the electrode assembly was disposed in a battery case for a secondary battery, and the prepared electrolyte solution was then injected into the case to prepare a lithium secondary battery of the present invention.

Example 2

A lithium secondary battery was prepared in the same manner as in Example 1 except that 3 g of the compound of Formula 1b, instead of the compound of Formula 1a, was included in 94 g of the mixed solution during the preparation of the electrolyte solution in Example 1.

Example 3

A lithium secondary battery was prepared in the same manner as in Example 1 except that 3 g of the compound of Formula 1c, instead of the compound of Formula 1a, was included in 94 g of the mixed solution during the preparation of the electrolyte solution in Example 1.

Example 4

A lithium secondary battery was prepared in the same manner as in Example 1 except that 7 g of the compound of Formula 1a was included in 90 g of the mixed solution during the preparation of the electrolyte solution in Example 1.

Example 5

A lithium secondary battery was prepared in the same manner as in Example 1 except that 0.1 g of the compound of Formula 1a was included in 96.9 g of the mixed solution during the preparation of the electrolyte solution in Example 1.

Example 6

A lithium secondary battery was prepared in the same manner as in Example 1 except that 5 g of the compound of Formula 1a was included in 92 g of the mixed solution during the preparation of the electrolyte solution in Example 1.

Comparative Example 1

A lithium secondary battery was prepared in the same manner as in Example 1 except that the compound of Formula 1a was not added during the preparation of the electrolyte solution in Example 1.

Comparative Example 2

A lithium secondary battery was prepared in the same manner as in Example 1 except that 0.03 g of the compound of Formula 1a was included in 96.97 g of the mixed solution during the preparation of the electrolyte solution in Example 1.

Comparative Example 3

A lithium secondary battery was prepared in the same manner as in Example 1 except that 8.0 g of the compound of Formula 1a was included in 89 g of the mixed solution during the preparation of the electrolyte solution in Example 1.

Comparative Example 4

A lithium secondary battery was prepared in the same manner as in Example 1 except that 8.0 g of the compound of Formula 1b was included in 89 g of the mixed solution during the preparation of the electrolyte solution in Example 1.

Comparative Example 5

A lithium secondary battery was prepared in the same manner as in Example 1 except that 0.03 g of the compound of Formula 1c was included in 96.97 g of the mixed solution during the preparation of the electrolyte solution in Example 1.

Experimental Examples

Experimental Example 1

Initial Resistance Measurement

After the lithium secondary batteries prepared in Examples 1 to 6 and Comparative Examples 1 and 5 were each charged to a state of charge (SOC) of 50% at 25° C. and then discharged at 3 C for 10 seconds, initial resistance was calculated from the voltage drop thus obtained.

The results thereof are presented in Table 1 below.

TABLE 1

|  | Additive | Amount (wt %) | Initial resistance (mΩ) |
|---|---|---|---|
| Example 1 | Formula 1a | 0.05 | 51 |
| Example 2 | Formula 1b | 3.0 | 53 |
| Example 3 | Formula 1c | 3.0 | 55 |
| Example 4 | Formula 1a | 7.0 | 60 |
| Example 5 | Formula 1a | 0.1 | 52 |
| Example 6 | Formula 1a | 5.0 | 62 |
| Comparative Example 1 | — | — | 50 |
| Comparative Example 2 | Formula 1a | 0.03 | 49 |
| Comparative Example 3 | Formula 1a | 8.0 | 75 |
| Comparative Example 4 | Formula 1b | 8.0 | 80 |
| Comparative Example 5 | Formula 1c | 0.03 | 50 |

Referring to Table 1, with respect to the secondary batteries of Examples 1 to 6 which included the electrolyte solutions for a lithium secondary battery including the additives of the present invention, since the SEI film stably formed during initial charge prevented an additional electrolyte decomposition reaction, there was very little voltage drop, and thus, it may be understood that initial resistance values were reduced to 62 mΩ or less.

In contrast, with respect to the secondary batteries of Comparative Examples 3 and 4 which respectively included the electrolyte solutions in which excessive amounts of the additives were contained, it may be understood that initial resistance values were significantly increased to 75 mΩ or more.

With respect to the secondary battery of Comparative Example 1, which included the electrolyte solution without the additive, and the secondary batteries of Comparative Examples 2 and 5 which respectively included the electrolyte solutions including trace amounts of the additives, since the amount of the additives were insignificant, it may be understood that initial resistance values were not significantly increased to about 50 mΩ or less.

Experimental Example 2

Measurement of Capacity Reduction after High-temperature Storage (60° C.)

After the lithium secondary batteries prepared in Examples 1 to 6 and Comparative Examples 1 and 5 were each charged to a SOC of 100% at 25° C. and then discharged at 0.5 C to 3.0 V to measure initial (discharge) capacity.

Subsequently, each lithium secondary battery was stored in a chamber at 60° C. for 4 weeks.

Thereafter, each lithium secondary battery was discharged at 0.5 C to 3.0 V at 25° C., charged at 0.5 C to a SOC of 100%, and again discharged at 0.5 C to 3.0 V to measure recovery (discharge) capacity.

Measurement results were compared with the initial capacities and the results thereof are presented in Table 2 below.

TABLE 2

| | Additive | Amount (wt %) | Initial capacity (mAh) | Recovery capacity after storage at 60° C. for 4 weeks (mAh) |
|---|---|---|---|---|
| Example 1 | Formula 1a | 0.05 | 759 | 635 |
| Example 2 | Formula 1b | 3.0 | 745 | 620 |
| Example 3 | Formula 1c | 3.0 | 755 | 640 |
| Example 4 | Formula 1a | 7.0 | 748 | 635 |
| Example 5 | Formula 1a | 0.1 | 765 | 650 |
| Example 6 | Formula 1a | 5.0 | 755 | 640 |
| Comparative Example 1 | — | — | 760 | 500 |
| Comparative Example 2 | Formula 1a | 0.03 | 761 | 480 |
| Comparative Example 3 | Formula 1a | 8.0 | 745 | 530 |
| Comparative Example 4 | Formula 1b | 8.0 | 740 | 550 |
| Comparative Example 5 | Formula 1c | 0.03 | 763 | 505 |

As illustrated in Table 2, with respect to the secondary batteries of Examples 1 to 6 which included the electrolyte solutions for a lithium secondary battery including the additives of the present invention, it may be understood that their recovery capacities were excellent at about 83% or more even after the high-temperature storage.

In contrast, with respect to the secondary battery of Comparative Example 1, which included the electrolyte solution without the additive, and the secondary batteries of Comparative Examples 2 and 5 which respectively included the electrolyte solutions including trace amounts of the additives, since recovery capacities were about 66% or less, it may be understood that the recovery capacities were lower than those of the secondary batteries of Examples 1 to 6.

Also, with respect to the secondary batteries of Comparative Examples 3 and 4 which respectively included the electrolyte solutions in which excessive amounts of the additives were contained, since recovery capacities were about 71% or less due to the occurrence of a side reaction caused by the additives, it may be understood that the recovery capacities were lower than those of the secondary batteries of Examples 1 to 6.

Experimental Example 3

Measurement of Gas Generation at High temperature (60° C.)

The lithium secondary batteries prepared in Examples 1 to 6 and Comparative Examples 1 and 5 were each charged to a SOC of 100% at 25° C.

Subsequently, each lithium secondary battery was stored in a chamber at 60° C. for 4 weeks, and a change in cell thickness due to gas generation during the storage period was checked.

The measured results are presented in Table 3 below.

TABLE 3

| | | | Cell thickness (mm) | |
|---|---|---|---|---|
| | Additive | Amount (wt %) | Initial | After storage at 60° C. for 4 weeks |
| Example 1 | Formula 1a | 0.05 | 4.21 | 5.02 |
| Example 2 | Formula 1b | 3.0 | 4.22 | 4.75 |
| Example 3 | Formula 1c | 3.0 | 4.19 | 5.08 |
| Example 4 | Formula 1a | 7.0 | 4.23 | 4.56 |
| Example 5 | Formula 1a | 0.1 | 4.20 | 4.95 |
| Example 6 | Formula 1a | 5.0 | 4.19 | 4.85 |
| Comparative Example 1 | — | — | 4.20 | 7.75 |
| Comparative Example 2 | Formula 1a | 0.03 | 4.25 | 7.70 |
| Comparative Example 3 | Formula 1a | 8.0 | 4.23 | 4.60 |
| Comparative Example 4 | Formula 1b | 8.0 | 4.28 | 4.62 |
| Comparative Example 5 | Formula 1c | 0.03 | 4.21 | 7.80 |

Referring to thickness change rates illustrated in Table 3, with respect to the secondary batteries of Examples 1 to 6 which included the electrolyte solutions for a lithium secondary battery including the additives of the present invention, it may be understood that thickness increase rates were low at about 21% or less even after storage at 60° C. for 4 weeks.

With respect to the secondary batteries of Comparative Examples 3 and 4 which respectively included the electrolyte solutions in which excessive amounts of the additives were contained, since the gas generation suppression effect was increased while an excessive amount of the SEI film was formed by the additives, it may be understood that the thickness increase rates after storage at 60° C. for 4 weeks were rather low at about 8% or less.

In contrast, with respect to the secondary battery of Comparative Example 1, which included the electrolyte solution without the additive, and the secondary batteries of Comparative Examples 2 and 5 which respectively included the electrolyte solutions including trace amounts of the additives, since an SEI film formation effect was insignificant, it may be understood that the thickness increase rates after storage at 60° C. for 4 weeks were high at about 80% or more.

The invention claimed is:

1. An electrolyte solution for a lithium secondary battery, the electrolyte solution comprising an electrolyte salt, an organic solvent, and an additive,
    wherein the additive comprises a compound represented by Formula 1:

[Formula 1]

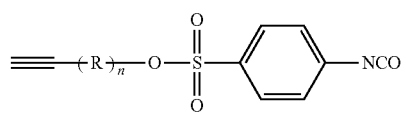

wherein, in Formula 1,
R is an alkylene group having 1 to 5 carbon atoms or an arylene group having 5 to 8 carbon atoms, and
n is an integer of 1 to 10.

2. The electrolyte solution for a lithium secondary battery of claim 1, wherein the compound represented by Formula 1 comprises at least one selected from the group consisting of compounds represented by Formulae 1a to 1c:

[Formula 1a]

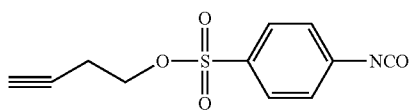

[Formula 1b]

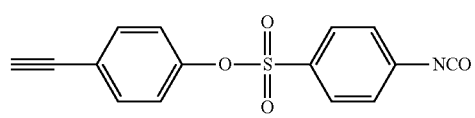

[Formula 1c]

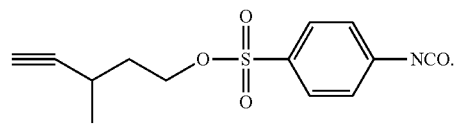

3. The electrolyte solution for a lithium secondary battery of claim 1, wherein the compound represented by Formula 1 is included in an amount of 0.05 wt % to 7 wt % based on a total weight of the electrolyte solution for a lithium secondary battery.

4. The electrolyte solution for a lithium secondary battery of claim 3, wherein the compound represented by Formula 1 is included in an amount of 0.1 wt % to 5 wt % based on the total weight of the electrolyte solution for a lithium secondary battery.

5. A lithium secondary battery comprising a positive electrode, a negative electrode, a separator disposed between the positive electrode and the negative electrode, and an electrolyte solution for a lithium secondary battery, wherein the electrolyte solution for a lithium secondary battery comprises the electrolyte solution for a lithium secondary battery of claim 1.

* * * * *